United States Patent

Bender et al.

[11] Patent Number: 4,485,240
[45] Date of Patent: Nov. 27, 1984

[54] PROCESS FOR THE PREPARATION OF OPTIONALLY-SUBSTITUTED 1,2,3,4-TETRAHYDRO-9-CYANOMETHYL-CARBAZOL-1-ONES

[75] Inventors: Heinz Bender, Frankfurt am Main; Veit Buch, Bad Vilbel; Rudi Beyerle, Frankfurt am Main; Klaus Kühlein, Kelkheim, all of Fed. Rep. of Germany

[73] Assignee: Cassella Aktiengesellschaft, Fed. Rep. of Germany

[21] Appl. No.: 487,020

[22] Filed: Apr. 19, 1983

[30] Foreign Application Priority Data

May 11, 1982 [DE] Fed. Rep. of Germany ....... 3217563

[51] Int. Cl.³ .................. C07D 209/86; C07D 209/88
[52] U.S. Cl. .................................................... 548/449
[58] Field of Search .......................,........................ 548/449

[56] References Cited

PUBLICATIONS

Mashkovskii et al., *Chemical Abstracts*, vol. 78, (1973), No. 4284d.

*Primary Examiner*—Robert W. Ramsuer
*Attorney, Agent, or Firm*—Berman, Aisenberg & Platt

[57] ABSTRACT

In a process for the preparation of optionally-substituted 1,2,3,4-tetrahydro-9-cyanomethylcarbazol-1-ones of the formula

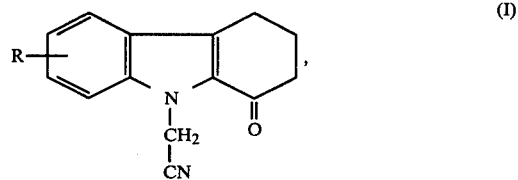

wherein R denotes hydrogen, halogen, alkyl or alkoxy, by cyano-methylating optionally substituted 1,2,3,4-tetrahydrocarbazol-1-ones of the formula

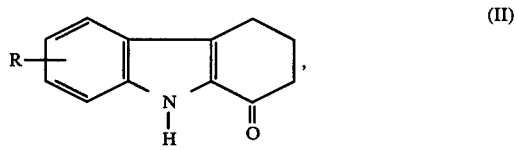

wherein R has the meanings mentioned above, the starting material of formula II is reacted, in a two-phase system consisting of water and a water-immiscible organic solvent, in the presence of a strong base and a known phase transfer catalyst, with a cyanomethylating agent of the formula

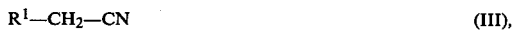

$R^1$—$CH_2$—CN       (III), wherein $R^1$ denotes halogen or a radical of the formula $R^2$—$SO_2$—O— and $R^2$ represents alkyl, phenyl or substituted phenyl.

8 Claims, No Drawings

PROCESS FOR THE PREPARATION OF OPTIONALLY-SUBSTITUTED 1,2,3,4-TETRAHYDRO-9-CYANOMETHYLCARBAZOL-1-ONES 1,2,3,4-Tetrahydro-9-cyanomethylcarbazol-1-ones of formula I

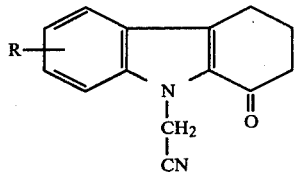

(I)

especially those in which R is in the 6-position of the carbazole system, are valuable intermediate products for the preparation of substances having a psychotropic action. Such compounds are known, for example, from German Offenlegungsschrift 2,824,447.5 and European Laid-Open Specification No. 28,270.

A process for the preparation of 1,2,3,4-tetrahydro-6-methyl-9-cyanomethylcarbazol-1-one in which 1,2,3,4-tetrahydro-6-methylcarbazol-1-one is converted into its N-metal derivative, for example into the N-sodium derivative, and the latter is alkylated by means of chloroacetonitrile in an organic solvent, is known from German Offenlegungsschrift 2,114,230. In this known process, the sodium salt is prepared by adding a suspension of sodium hydride or an alcoholic solution of a sodium alcoholate to a solution of the 1,2,3,4-tetrahydro-6-methylcarbazol-1-one in an anhydrous organic solvent, such as dioxane, dimethylformamide, benzene or the like. If sodium hydride is used, hydrogen is evolved; if a sodium alcoholate is used, the corresponding alcohol is liberated and must be removed by distillation. After the sodium derivative has been formed, chloroacetonitrile is added to the reaction mixture. Significant yields of the desired end product are only obtained in this known process if the organic solvent employed is a dipolar aprotic solvent, such as dimethylformamide, and if the reaction is carried out with the rigorous exclusion of water. Dipolar aprotic solvents, such as the said dimethylformamide, are, however, relatively expensive, they are difficult to recover and (to avoid damage to the environment) they must on no account reach the effluent. The purity of the product prepared by the known process also leaves something to be desired. To prepare it in a purity required for further processing to pharmaceutical products, the cyanomethylation must be followed by a purification operation, which cannot be carried out without losses. In the case of fairly small batches, therefore, maximum yields of pure substance of 45% of theory are obtained by the known process; in the case of fairly large batches, which require a longer reaction time, the yields of pure substance fall to 30% of theory or less.

It has now been found that optionally substituted 1,2,3,4-tetrahydro-9-cyanomethylcarbazol-1-ones of formula I

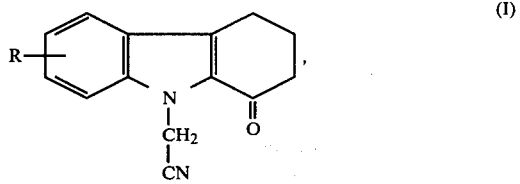

(I)

wherein R denotes hydrogen, halogen, alkyl or alkoxy, are obtained in a high yield and in excellent purity if, in the cyanomethylation of optionally substituted 1,2,3,4-tetrahydrocarbazol-1-ones of formula II

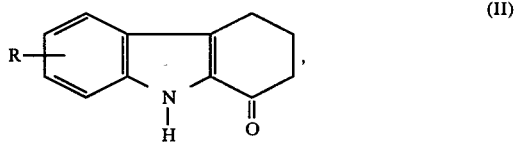

(II)

wherein R has the meaning mentioned above, the starting material of the formula II is reacted with a cyanomethylating agent of formula III

$$R^1-CH_2-CN \quad (III)$$

[wherein $R^1$ denotes halogen or a radical of the formula $R^2$—$SO_2$—O— and $R^2$ represents alkyl, phenyl or substituted phenyl,] in a two-phase system, consisting of water and a water-immiscible organic solvent, in the presence of a strong base and a known phase transfer catalyst.

The reactants in the process according to the invention, the tetrahydrocarbazole derivative of formula II, the alkylating agent of formula III and the base can, in principle, be reacted together in a 1:1:1 molar ratio.

However, in order to achieve as complete cyanomethylation of the carbazole derivative as possible, it is advantageous to employ an excess of 5 to 30 mol %, preferably 10 to 20 mol %, of the cyanomethylating agent. The base present in the cyanomethylation reaction is also employed in an excess of 2 to 20 fold, preferably 5 to 10 fold, relative to the carbazole derivative. In principle, it would also be possible to employ any desired greater excess of cyanoalkylating agent and base; however, no further economic advantages are achieved thereby, since the slight possible increase in yield no longer compensates for the higher input and the more complicated working up.

In the optionally substituted 1,2,3,4-tetrahydro-9-cyanomethylcarbazol-1-ones of formula I which can be prepared in accordance with the invention, a halogen represented by R is a fluorine, chlorine, bromine or iodine atom, preferably a fluorine, chlorine or bromine atom.

Alkyl or alkoxy groups represented by R are linear or branched and have 1 to 8, preferably 1 to 4, C atoms. Furthermore, it is preferable to prepare, by the process according to the invention, 1,2,3,4-tetrahydro-9-cyanomethylcarbazol-1-ones in which R is not hydrogen, that is to say those which have a substituent in the aromatic benzene nucleus of the tetrahydrocarbazole system, particularly if this substituent is in the 6-position of the carbazole skeleton.

In the cyanomethylating agent of formula III employed in the process according to the invention, $R^1$ denotes, in general, a radical which can be split off readily as an anion in the presence of a base. Halogen atoms, such as chlorine, bromine or iodine, or radicals of the formula $R^2-SO_2-O-$ wherein $R^2$ represents alkyl, phenyl or substituted phenyl, have proved particularly suitable for $R^1$.

It is particularly advantageous to employ cyanomethylating agents of formula III in which $R^1$ denotes chlorine, bromine or a radical of the formula $R^2-SO_2-O-$ wherein $R^2$ represents alkyl having 1 to 5 C atoms, phenyl or phenyl which is substituted by chlorine or alkyl having 1 to 4 C atoms. Cyanomethylating agents which are particularly preferred for the process according to the invention are chloroacetonitrile, cyanomethyl phenylsulphonate and cyanomethyl p-toluenesulphonate.

Carrying out the reaction in a two-phase system consisting of water and an organic solvent is an essential characteristic of the process according to the invention. Suitable organic solvents are water-immiscible solvents which behave in an inert manner under the reaction conditions, that is to say do not interfere adversely with the reaction. Examples of solvents which are suitable for the process according to the invention are aliphatic, cycloaliphatic or aromatic hydrocarbons and aromatic halogenated hydrocarbons and higher-boiling ethers or polyethers, provided they are not miscible with the aqueous phase containing the dissolved base. Examples of solvents of this type are petroleum fractions, such as petroleum ether, gasoline, ligroin or heavy naphtha, cyclohexane, benzene, toluene, o-, m- or p-xylene or technical mixtures of isomers of the latter, monochlorobenzene, o- dichlorobenzene or dimethoxyethane. It is also possible to use mixtures of the said solvents with one another. The use of toluene or technical mixtures of xylene isomers is particularly preferred.

The two-phase system consisting of water and a water-immiscible organic solvent should contain sufficient organic solvent to achieve an adequately high reaction rate, as a result of the reaction of the portions of the starting materials II and III dissolved therein, and thereby a satisfactory time of reaction for the whole batch. It is advantageous to employ sufficient organic solvent to dissolve the bulk of the tetrahydrocarbazolone of formula II, preferably to dissolve it completely. The quantity of water should be sufficient to dissolve the base added and to keep in solution, substantially or completely, any salt which may be formed, for example alkali metal benzenesulphonate or toluenesulphonate. As a rule, the quantity by weight of organic solvent employed will be up to 30 times, preferably 10 to 20 times, the quantity by weight of the tetrahydrocarbazolone of formula II. The ratio by weight of organic solvent to water varies between 1:0.2 and 1:2, preferably between 1:0.4 and 1:0.7.

The cyanomethylation reaction of the process according to the invention is carried out in the presence of a base. This base has the function of initiating the detachment of the radical $R^1$, in the form of an anion, from the cyanomethylating agent of formula III and of capturing the proton liberated in the reaction. Suitable bases are compounds which produce a pH value greater than 10 in a molar aqueous solution. Examples of such bases are alkali-metal salts, and to a certain extent also alkaline-earth-metal salts, of weak and very weak inorganic and organic acids, such as alkali-metal carbonates, trialkali-metal phosphates or alkali-metal borates and alkali-metal hydroxides and, to a certain extent, also alkaline-earth-metal hydroxides. Bases which are preferred for the process according to the invention are alkali-metal hydroxides, in particular sodium hydroxide or potassium hydroxide.

A further characteristic of the process according to the invention is the use of known phase-transfer catalysts. A summarising survey on phase transfer catalysis and catalysts is to be found, for example, in the article by E. V. Dehmlow in "Angewandte Chemie" International Edition in English, Volume 13, page 170 (1974).

Phase-transfer catalysts which are suitable for carrying out the process according to the invention are, in particular, quaternary ammonium or phosphonium salts of formulae IV and V:

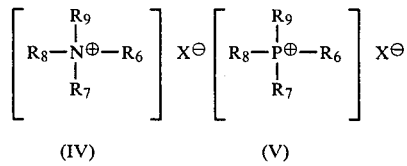

In these formulae, $R_6$ to $R_9$ denote alkyl having 1 to 16 C atoms, hydroxyalkyl having 2 to 16 C atoms, preferably 2 to 4 C atoms, or alkoxyalkyl having 1 to 16 C atoms, preferably 2 to 6 C atoms, aryl, especially phenyl, alkylphenyl having 1 to 10 C atoms in the alkyl radical, or aralkyl, such as benzyl or phenethyl, and $X^-$ denotes the ions $F^-$, $Cl^-$, $Br^-$, $SO_4^{--}$, $HSO_4^-$, $SO_3^{--}$ and $HSO_3^-$.

Examples of phase transfer catalysts which are particularly suitable for the purpose of use according to the invention are di(dodecyl)-dimethylammonium chloride, hexadecyltrimethylammonium chloride, tetrabutylammonium chloride, trioctylmethylammonium chloride, trisdecylmethylammonium chloride, trialkyl-($C_8$–$C_{10}$ mixture)-methylammonium chloride, tetrabutylammonium bisulphate, benzyltrimethylammonium chloride and similar compounds. Examples of the cations of further known phase transfer catalysts are tetrapropylammonium, tetradodecylammonium, benzyltriethylammonium, trihexylmethylammonium, cetyltrimethylammonium and n-alkyltriethylammonium in which the alkyl radical has 4 or more, for example 6, C atoms, trioctylmethylammonium, tricaprylylmethylammonium and hexadecyltributylphosphonium. Suitable anions for these cations are, in particular, bisulphate, chloride and bromide.

Trialkyl-($C_8$–$C_{10}$-mixture)-methylammonium chloride and tetrabutylammonium chloride and tetrabutylammonium bisulphate are preferred for use according to the invention. The quantity of phase transfer catalyst to be employed is advantageously 1 to 10 mol %, relative to the quantity of aromatic aminohydroxy compound employed. It is preferable to employ 2 to 6 mol % of the phase transfer catalyst.

The cyanomethylation reaction on which the process according to the invention is based takes place smoothly and completely under the process conditions according to the invention at temperatures as low as room temperature. The process according to the invention is, therefore, preferably carried out at temperatures from 10° to 30° C. If it is desired for special reasons to accelerate the reaction further, this can be effected in a known manner by warming the reaction mixture. In this event, it is advantageous to select a reaction temperature below the boiling point of the water-immiscible organic solvent. One possibility is to carry out the reaction at the boiling point of the azeotrope of the organic solvent and water. Normally, adequate acceleration of the reaction is achieved merely by warming to a maximum of 50° C. The reaction can also be carried out with good yields below 10° C., if a correspondingly longer reaction time is accepted.

The process according to the invention can be carried out by introducing the whole of the reactants, the tetrahydrocarbazolone of formula II, the cyanomethylating agent of formula III and the base, in any desired sequence, into the previously-taken solvent system consisting of water and organic solvent-advantageously with thorough and continuous mixing—and keeping the mixture at the desired temperature, with thorough mixing, until the reaction is complete. In view of saponification reactions, it can be advantageous to add the cyanomethylating agent or the base or both components to the reaction mixture gradually, in portions, or continuously.

A particularly advantageous embodiment of the process according to the invention is effected when cyanomethyl phenylsulphonate or tolylsulphonate is employed as the cyanomethylating agent. This embodiment consists in using the said cyanomethylating agent not in an isolated, pure form, but in the form of a crude dispersion produced in the preparation thereof. This variant can also be carried out as a "one-pot reaction" by first preparing, in a known manner [compare, for example, Lichtenberger, Bull. Soc. Chim. France (1948), pages 995–1,001], a dispersion of the said cyanomethyl ester from benzenesulphochloride or p-toluenesulphochloride, formaldehyde and an alkali-metal cyanide in an aqueous medium in an adequately large reaction vessel, and, without isolating this cyanomethyl ester, adding to the dispersion a solution of the 1,2,3,4-tetrahydrocarbazol-1-one derivative of formula II in the organic solvent, preferably toluene or xylene. After the phase-transfer catalyst has been added, the reaction is carried out by adding dropwise the aqueous solution of the base, preferably dilute sodium hydroxide solution. Apart from the saving in time and materials, this procedure has the advantage of avoiding any contact of the works personnel with the alkylating agents of formula III, which are not completely harmless from the point of view of health.

When the cyanomethylation reaction is complete, any excess of the cyanomethylating agent of formula III which may still be present is saponified by the excess of base present in the system.

The compounds of formula I which have been prepared in accordance with the invention are isolated in a manner which is in itself known.

If, when using a relatively small quantity of organic solvent, the end product is precipitated, the latter can be filtered off without further treatment and freed from excess base and salts by washing with water.

If sufficient organic solvent has been employed to dissolve the organic compounds completely, the procedure followed after the conclusion of the reaction, is for example, to separate the organic phase from the aqueous phase and to concentrate the former, advantageously under reduced pressure, until the end product is precipitated. If necessary, concentrating the solution can, of course, be preceded by filtering off impurities, washing and/or drying procedures or other known working up procedures. Other known routes to the isolation of the end product can, of course, also be followed. Thus, after a coarse separation of phases, the organic phase can be distilled, the water still present therein being removed as an azeotrope. Impurities can be removed by filtration when the water and the necessary quantity of organic solvent have been distilled off. The end product can be induced to crystallise out by cooling the filtrate. In this procedure the products are, as a rule, obtained in such a pure state that further purification operations are superfluous.

The following illustrative embodiments illustrate the process according to the invention.

EXAMPLE 1

A suspension of 1.1 mols of cyanomethyl benzenesulphonate is prepared by the method of Lichtenberger, Bull. Soc. Chim. France (1948), page 998, from benzenesulphochloride, formaldehyde and sodium cyanide in 230 ml of water, and 4,000 ml of toluene, 20 g of tetrabutylammonium bisulphate and 199 g (1 mol) of 1,2,3,4-tetrahydro-6-methylcarbazol-1-one are added thereto. 1,180 ml (10 mols) of sodium hydroxide solution are added dropwise at 20°–25° C. in the course of 10–20 minutes, while stirring vigorously. After 1 hour the precipitated sodium benzenesulphonate is filtered off with suction. The filtrate is allowed to stand, and the organic and aqueous phases are separated from one another in a separating funnel. The toluene layer is washed with acidified water and evaporated, and the residue is recrystallised from ethanol. Yield: 214 g=90% of theory, melting point 140°.

EXAMPLE 2

199 g (1 mol) of 1,2,3,4-tetrahydro-6-methylcarbazol-1-one, 4,000 ml of toluene, 1,180 ml (10 mols) of sodium hydroxide solution and 20 g of tertiarybutylammonium bisulphate and initially taken at 20°–25° C., and the mixture is stirred for 30 minutes. 91 g (1.2 mols) of chloroacetonitrile are then added dropwise at 20°–25° C. in the course of 2 hours and stirring is then continued for a further 10 minutes. After the mixture has been allowed to settle and the phases have been separated, the toluene layer is washed with acidified water and evaporated. The residue is recrystallised from ethanol.

The yield of 1,2,3,4-tetrahydro-6-methyl-9-cyanomethylcarbazol-1-one is 190 g (~80% of theory), melting point 138°–139° C.

The following are also obtained in very good yields if equivalent quantities of other 1,2,3,4-tetrahydrocarbazol-1-ones of formula II, which are substituted in the 6-position by chlorine, bromine, fluorine or methoxy, are employed as the starting material instead of the 1,2,3,4-tetrahydro-6-methylcarbazol-1-one employed in Examples 1 and 2, the reaction being carried out in other respects as indicated in the examples:

1,2,3,4-Tetrahydro-6-chloro-9-cyanomethylcarbazol-1-one, melting point: 159° C.

1,2,3,4-Tetrahydro-6-bromo-9-cyanomethylcarbazol-1-one, melting point: 180°–181° C.

1,2,3,4-Tetrahydro-6-fluoro-9-cyanomethylcarbazol-1-one, melting point: 136° C.

1,2,3,4-Tetrahydro-6-methoxy-9-cyanomethylcarbazol-1-one, melting point: 138° C.

What is claimed is:

1. A process for the preparation of optionally-substituted 1,2,3,4-tetrahydro-9-cyanomethylcarbazol-1-one of formula I

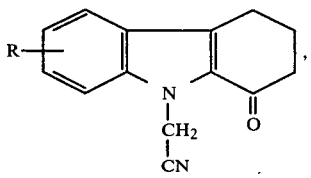

wherein R denotes hydrogen, halogen, alkyl or alkoxy, by cyanomethylating an optionally-substituted 1,2,3,4-tetrahydrocarbazol-1-one of the formula

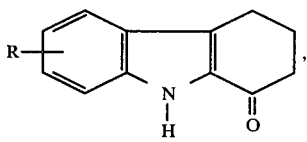

wherein R has the meaning mentioned above, characterized in that the starting material of formula II is reacted, in a two-phase system consisting of water and a water-immiscible organic solvent, in the presence of a strong base and a known phase-transfer catalyst, with a cyanomethylating agent of formula

wherein $R^1$ denotes halogen or a radical of the formula $R^2$—$SO_2$—O— and $R^2$ represents alkyl, phenyl or substituted phenyl.

2. A process according to claim 1 for preparing a 1,2,3,4-tetrahydro-9-cyanomethylcarbazol-1-one of formula I wherein R denotes hydrogen, fluorine, chlorine, bromine, alkyl having 1 to 8 C atoms or alkoxy having 1 to 8 C atoms, characterised in that a 1,2,3,4-tetrahydrocarbazol-1-one of formula II, in which R has the meaning mentioned herein, is employed.

3. A process according to claim 1 for the preparation of a 1,2,3,4-tetrahydro-9-cyanomethylcarbazol-1-one of formula I, wherein R denotes hydrogen, fluorine, chlorine, bromine, alkyl having 1 to 4 C atoms or alkoxy having 1 to 4 C atoms, characterised in that a 1,2,3,4-tetrahydrocarbazol-1-one of formula II, in which R has the meanings mentioned herein, is employed.

4. A process according to claim 1 or 3 for the preparation of a 1,2,3,4-tetrahydro-9-cyanomethylcarbazol-1-one of formula I wherein R is not hydrogen.

5. A process according to claim 4, characterised in that R is in the 6-position of the carbazole system.

6. A process according to claim 1 or 2, characterised in that a cyanomethylating agent of formula III, wherein $R^1$ denotes chlorine, bromine, iodine or a radical of the formula $R^2$—$SO_2$—O— and $R^2$ represents alkyl having 1 to 18 C atoms, phenyl or phenyl which is substituted by halogen, lower alkyl or lower alkoxy, is employed.

7. A process according to claim 6, characterised in that a cyanomethylating agent of formula III, wherein $R^1$ denotes chlorine, bromine or a radical of the formula $R^2$—$SO_2$—O— and $R^2$ represents alkyl having 1 to 5 C atoms, phenyl or phenyl which is substituted by chlorine or lower alkyl, is employed.

8. A process according to claim 1, characterized in that a cyanomethylating agent of formula III, wherein $R^1$ denotes a radical of the formula $R^2$—$SO_2$—O— and $R^2$ represents phenyl or phenyl which is substituted by lower alkyl, is employed, without intermediate isolation, in the form of a crude dispersion produced in the preparation thereof.

* * * * *